United States Patent [19]

Buckle et al.

[11] 3,936,504
[45] Feb. 3, 1976

[54] ANTI-ALLERGIC PHARMACEUTICAL COMPOSITIONS

[75] Inventors: Derek Richard Buckle, Redhill; Harry Smith, Maplehurst, near Horsham, both of England

[73] Assignee: Beecham Group Limited, United Kingdom

[22] Filed: Dec. 21, 1972

[21] Appl. No.: 317,296

[30] Foreign Application Priority Data

Jan. 25, 1972  United Kingdom................. 3348/72
Mar. 22, 1972  United Kingdom............... 13300/72
June 20, 1972  United Kingdom............... 28707/72
Oct. 18, 1972  United Kingdom............... 48027/72

[52] U.S. Cl....... 260/590 D; 260/343.3 R; 260/469; 260/297 B; 424/263; 424/331
[51] Int. Cl.$^2$............... C07C 49/76; C07C 49/80; C07C 49/84
[58] Field of Search .................................. 260/590

[56] References Cited
OTHER PUBLICATIONS
Chemical Abstracts Index, Vol. 76, 1808cs.
Chemical Abstracts Index, Vol. 76, 1808cs and 1809cs.
Chemical Abstracts Index, Vol. 72, 1928s.
Chemical Abstracts Index, Vol. 73, 1872s.
Cema et al., Chem. Abstracts, 72, 132349s, (1970).
O. Sadchii et al., Chem. Abstracts, 73, 120381d, (1970).
Cema et al., (I), Chem. Abstracts, 70, 375075s, (1969).
Oskaja et al., Chem. Abstracts, 76, 24943e, (1972), (cites 1971 article).
Eglite et al., Chem. Abstracts, 75, 29752f, (1971).
Cema et al., (II), Chem. Abstracts, 76, 153401a, (1972), (cites 1970 article).
Cema et al., (III), Chem. Abstracts, 76, 153397d, (1972).
Stradins et al., Chem. Abstracts, 56, 8461f, (1962).

*Primary Examiner*—D. Horwitz

[57] ABSTRACT

2-Nitroindane-1,3-dione derivatives are useful in the prophylaxis and treatment of asthma, hay fever and also in the treatment of rhinitis.

21 Claims, No Drawings

ANTI-ALLERGIC PHARMACEUTICAL COMPOSITIONS

This invention relates to pharmaceutical compositions which are useful in the inhibition of the effects of certain types of antigen-antibody reactions, and are therefore useful in the prophylaxis and treatment of diseases associated with allergic or immunological reactions, e.g. certain types of asthma and hay-fever, and also in the treatment of rhinitis.

We have discovered that certain derivatives of 2-nitroindane-1,3-dione have useful activity in warm-blooded mammals in that they inhibit the effects of certain types of antigen-antibody reactions. In particular, they appear to inhibit the release of mediator substances, such as histamine, which are normally released after antigen-antibody combinations and which normally mediate the allergic response. The class of 2-nitroindane-1,3-dione derivatives which we have found to be active in this way has formula (I):

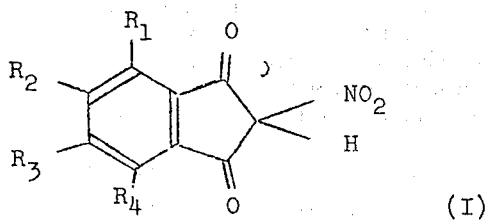

and the salts of compounds (I) are also active. In formula (I), $R_1$, $R_2$, $R_3$, and $R_4$ are each hydrogen or alkyl, alkoxy, aryl, aralkyl, heterocyclic or halogen groups, or any two adjacent groups $R_1$ and $R_2$, $R_2$ and $R_3$, or $R_3$ and $R_4$ taken together represent the residue of a substituted or unsubstituted carbocyclic or heterocyclic ring system. However, a search of the chemical literature has revealed that not all of the members of class (I) are novel compounds. Below we list those compounds of formula (I) which are mentioned in the literature, together with the appropriate literature reference:

- (I): $R_1 = R_2 = R_3 = R_4 = H$
- (I): $R_1 = R_2 = OCH_3$; $R_3 = R_4 = H$ Chem.Abs. 1961, 55, 476g
- (I): $R_2 = OCH_3$; $R_1 = R_3 = R_4 = H$ Chem.Abs. 1968, 68, 87034q
- (I): $R_1 = Cl$; $R_2 = R_3 = R_4 = H$ Chem.Abs. 1969, 70, 11379b
- (I): $R_2 = Cl$; $R_1 = R_3 = R_4 = H$ Chem.Abs. 1969, 70, 37507s
- (I): $R_2 = Br$; $R_1 = R_3 = R_4 = H$ Chem.Abs. 1972, 132349s
- (I): $R_1 = CH_3$; $R_2 = R_3 = R_4 = H$ Latv. PSR Zinat Akad, Vestis (Khim Ser) 1971, 425–30
- (I): $R_2 = I$; $R_1 = R_3 = R_4 = H$ ibid 1971, 179–181

In the above list, no reference has been given for the first compound, i.e. 2-nitroindane-1,3-dione itself which is, of course, a common laboratory reagent.

Although the above compounds are reported in the literature, no form of useful biological activity has been ascribed to them. Likewise there has been in the literature no suggestion that such compounds are likely to possess any form of useful biological activity, and in particular the discovery that they have anti-allergic activity has not been predicted in any way.

Accordingly, the present invention provides in its broadest aspect, a pharmaceutical composition comprising a compound of formula (I) or a pharmaceutically acceptable salt thereof:

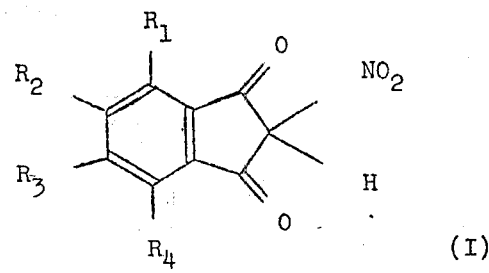

together with one or more pharmaceutically acceptable carriers, in which formula $R_1$, $R_2$, $R_3$ and $R_4$ represent hydrogen, lower alkyl, lower alkoxy, aryl, aralkyl, heterocyclic or halogen groups, and any two adjacent groups $R_1$ and $R_2$, and $R_3$ or $R_3$ and $R_4$ may be joined in a carbocyclic or heterocyclic ring system, this definition of $R_1$, $R_2$, $R_3$ and $R_4$ being subject to the proviso that $R_1$, $R_2$, $R_3$ and $R_4$ are not simultaneously hydrogen.

It will be noted that the above definition of the compositions of this invention specifically excludes compositions 2-nitroindane-1,3-dione itself. This exclusion is necessary since such compositions are claimed in a different pending patent application commonly assigned.

The compositions of this invention may be presented as a microfine powder for insufflation, e.g. as a snuff or in capsules of hard gelatine. They may also be presented together with a sterile liquid carrier for injection. Some of the compounds of formula (I) appear to be active when given by the oral route and thus the compositions of this invention may be in the form of tablets, capsules, pills or syrups. Preferably the compositions of this invention are presented in unit dosage form, or in a form in which the patient can administer to himself a single dosage. If desired, a small amount of bronchodilator compound may be incorporated in the compositions of the invention, both to inhibit the cough response if the composition is insufflated and to provide immediate relief during an asthmatic attack. The effective dose of compound (I) depends on the particular compound employed, but is generally in the range of from 0.1 mg/kg/day to 100 mg/kg/day.

The precise nature of the pharmaceutical carrier used in the composition of this invention is not important. Standard pharmaceutical practice may be followed, but it is perhaps worth noting that if the composition is to be administered by insufflation, a microfine powder where substantially all the particles have diameters of less than 50 microns is preferred.

The present invention also provides, in another of its aspects compounds of formula (I) and salts thereof:

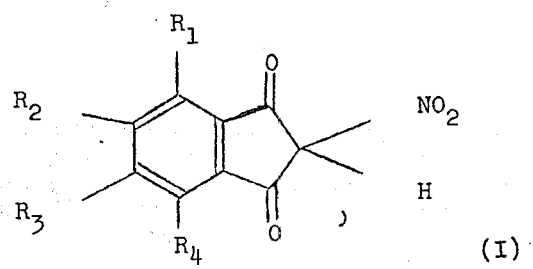

wherein $R_1$, $R_2$, $R_3$ and $R_4$ are each hydrogen or alkyl, alkoxy, aryl, aralkyl, heterocyclic or halogen groups, or any two adjacent groups, $R_1$ and $R_2$, $R_2$ and $R_3$, $R_3$ and $R_4$ may be joined in a carbocyclic or heterocyclic ring system, with the exception of the following compounds and salts thereof:

2-nitroindane-1,3-dione
4,5-dimethoxy-2-nitroindane-1,3-dione
5-methoxy-2-nitroindane-1,3-dione
4-chloro-2-nitroindane-1,3-dione
5-chloro-2-nitroindane-1,3-dione
5-bromo-2-nitroindane-1,3-dione
4-methyl-2-nitroindane-1,3-dione
5-iodo-2-nitroindane-1,3-dione Hereafter in this specification when the phrase "the compounds of this invention" is used, it is to be understood that we mean compounds of formula (I) and salts thereof excluding the eight compounds specifically listed above, and their salts.

Examples of groups $R_1$, $R_2$, $R_3$ and $R_4$ which may be present in the compounds of this invention include methyl, ethyl, n- and iso-propyl, n-, sec- and tert- butyl; methoxy, ethoxy, n- and iso- propoxy, n-, sec- and tert-butoxy, phenyl, benzyl, pyridyl, fluoro, chloro, bromo or iodo groups. In addition $R_1$ and $R_2$ and $R_2$ and $R_3$ or $R_3$ and $R_4$ taken together may represent the residue of a 1,2-phenylene or 1,2-cyclohexylene ring, which may carry one or more of the substituents listed above.

Compounds of the present invention which are especially preferred for their high activity include the following compounds and their pharmaceutically acceptable salts:

5,6-dimethyl-2-nitroindane-1,3-dione;
2-nitrobenz[f]indane-1,3-dione;
4-methoxy-6-ethyl-2-nitroindane-1,3-dione;
4-n-butoxy-2-nitroindane-1,3-dione;
4,6-dimethyl-2-nitroindane-1,3-dione;
5-methyl-2-nitroindane-1,3-dione;
4-fluoro-2-nitroindane-1,3-dione;

In the preceeding paragraphs, we have referred to pharmaceutically acceptable salts of the compounds of formula (I). Such salts include the alkali metal salts e.g. sodium or potassium, and salts with organic bases such as amines or amino compounds. These compounds may, on occasions, be capable of existing in an anhydrous form or one or more hydrates. The invention includes all of these forms.

The compounds of this invention may be prepared by a process which comprises nitrating the parent indane-1,3-dione of formula (III):

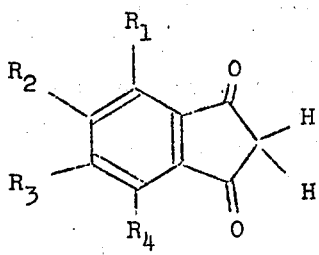

(III)

wherein $R_1$, $R_2$, $R_3$ and $R_4$ are as hereinbefore defined. The nitration step may be carried out at various temperatures although usually below 25°C. In general a temperature range of from −20°C to +20°C will be suitable, with +10°C being preferred.

The starting materials of formula (III) above may be prepared by known methods, the choice of method being dependent on the nature of the substituents present. With a single relatively chemically inert substituent such as a methyl, methoxy, or phenyl radical, the method of choice is the Claisen condensation wherein a compound of formula (IV):

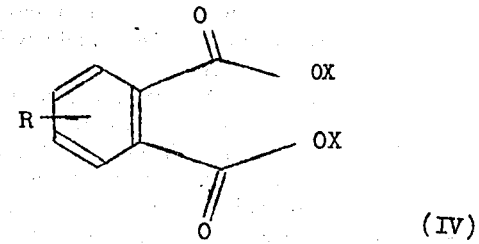

(IV)

wherein R is the inert substituent and X is an alkyl group is reacted with ethyl acetate.

With alkyl or alkoxy substituents in both the 3- and 6-position of (IV) the Claisen condensation may sometimes afford only low yields of the required diones and the same is true for the 4,5-methylenedioxy analogue. In such cases the preferred method involves the reaction of a compound formula (V), formed from the appropriate anhydride and acetic anhydride

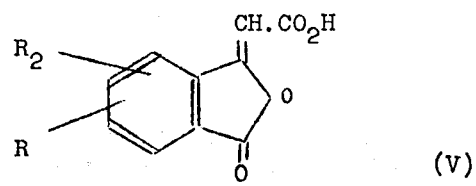

(V)

wherein both $R_1$ and $R_2$ are 4- or 7 - alkyl or alkoxy groups or $R_1$ $R_2$ is a 5,6-methylenedioxy group with a strong base such as sodium methoxide.

Neither of the above procedures is advisable in the presence of halogen functions, and here the Knoevenagel reaction is best suited. This involves the reaction of an active methylene compound with a compound of formula (VI):

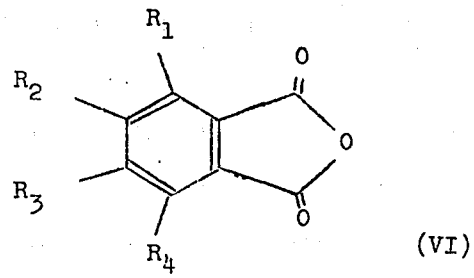

(VI)

wherein $R_1$, $R_2$, $R_3$ and $R_4$ are the same or different and each is hydrogen or a halogen group. The use of ethyl acetoacetate as the active methylene compound is most convenient (and economical) but has led to difficulties with both the 4-bromo and tetrachloro compounds, in which the carbethoxy intermediates are isolated ( (VII) and (VIII) respectively)

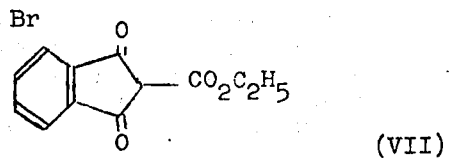

(VII)

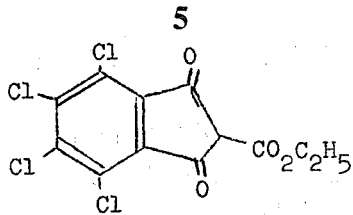

(VIII)

For this reason, ethyl acetoacetate has been replaced by the more easily removable t-butyl acetoacetate with complete success.

The following Examples illustrate the preparation of some of the compounds of this invention (and also a few of the previously known compounds listed above) and illustrate the biological activity of such compounds.

EXAMPLE 1 a. 4-Methyl indane-1,3-dione

To a 50% dispersion of sodium hydride in mineral oil (8.2 g; 0.17 mole of NaH) was added a solution of diethyl 3-methyl phthalate (28 g; 0.119 mole) in ethyl acetate (40 ml) and the mixture refluxed with occasional swirling on a steam bath for 4 hr. After cooling, the bright yellow sodium salt was filtered and washed with a little cold ethyl acetate. To the dried sodium salt (ca 27.2 g) was added rapidly a hot (80°C) solution of hydrochloric acid (48 ml) in water (480 ml) and the product kept at 70°C until decarboxylation ceased (7 mins), cooled to 5°C, and the pale yellow solid filtered and washed with water. Recrystallisation from benzene afforded a pale yellow crystalline solid, m.p. 125°–8°C. (Found; C, 75.38; H, 5.04; $C_{10}H_8O_2$ requires; C, 74.99; H, 5.03%).

b. 4-Methyl-2-nitroindane-1,3-dione

To a stirred suspension of 4-methyl-1,3-indanedione (1.02g.0.006 mole) in anhydrous ether (5 ml) at ca 10°C was added dropwise and with stirring fuming nitric acid (2.0 ml). After 10 mins. a clear, dark solution formed followed by precipitation of a bright yellow solid. The mass was filtered and washed with 5N hydrochloric acid. Recrystallisation from water/hydrochloric acid afforded the title compound, m.p. 108°–9°C. (Found; C, 56.16; H, 3.74; N, 6.32; $C_{10}H_7NO_4.1/2H_2O$ requires; C, 56.07; H, 3.76; N, 6.54%).

EXAMPLE 2 a. 5-Methyl indane-1,3-dione

This was prepared as in Example 1(a) from diethyl 4-methyl phthalate, m.p. (benzene) 114°–116°C. (Found; C, 75.04; H, 5.19; $C_{10}H_8O_2$ requires; C, 74.99; H, 5.03%).

b. 5-Methyl-2-nitroindane-1,3-dione

Nitration of 5-methyl indane-1,3-dione as in Example 1(b) yeilded the nitro product, m.p. (water/hydrochloric acid) 115°–117°C. (Found; C, 58.43; H, 3.39; N, 6.86; $C_{10}H_7NO_4$ requires; C, 58.54; H, 3.44; N, 6.83%).

EXAMPLE 3 a. 4-Methoxy indane-1,3-dione

Dimethyl-3-methoxy phthalate (13.8 g; 0.062 mole) in ethyl acetate (20 ml) was added to a 50% dispersion of sodium hydride in mineral oil (4.1 g; 0.085 mole of NaH) and the mixture refluxed for 4 hr. in a water bath. After cooling the red oil was treated with water and the yellow solid filtered and washed well with cold water. The sodium salt (15.8 g) was decarboxylated with 5N hydrochloric acid (23 ml) at 70°C. M.p. (benzene) 145°–147°C (d). (Found; C, 68.22; H, 4.63; $C_{10}H_8O_3$ requires; C, 68.18; H, 4.58%).

b. 4-Methoxy-2-nitro indane-1,3-dione

Nitration of 4-methoxy indane-1,3-dione as in Example 1(b) afforded the title compound, m.p. (water, hydrochloric acid) 132°–4°C. (Found; C, 54.39; H, 3.22; N, 6.42; $C_{10}H_7NO_5$ requires; C, 54.32; H, 3.19; N, 6.33%).

EXAMPLE 4 a. 4-Ethoxy indane-1,3-dione

Dimethyl 3-ethoxy phthalate (m.p. 58°C) was converted into 4-ethoxy indane-1,3-dione according to Example 1(a), m.p. (benzene) 111°C. (Found; C, 69.48; H, 5.34; $C_{11}H_{10}O_3$ requires; C, 69.46; H, 5.30%).

b. 4-Ethoxy-2-nitro indane-1,3-dione

Direct nitration of 4-ethoxy indane-1,3-dione with fuming nitric acid as in Example 1(b) gave the 2-nitro derivative, m.p. (water, hydrochloric acid) 95°–96°C. (Found; C, 48.83; H, 4.81; N, 4.97; $C_{10}H_9 NO_5. 2H_2O$ requires; C, 48.71; H, 4.83; N, 5.17%).

EXAMPLE 5 a. Benz[f] indane-1,3-dione

This was prepared by an analagous procedure to that described in Example 1(a), m.p. 136°C (d) from benzene. (Found; C, 73.80; H, 4.15; $C_{13}H_8O_2.H_2O$ requires; C, 72.89; H, 4.71%).

b. 2-Nitro benz[f]indane-1,3-dione

Nitration of benz[f] indane-1,3-dione with fuming nitric acid in ether at 10°C afforded the title compound, m.p. (water, hydrochloric acid) 163°–4°C. (Found; C, 64.89; H, 3.06; N, 5.03; $C_{13}H_7 NO_4$ requires; C, 64.74; H, 2.93; N, 5.81%).

EXAMPLE 6 a. 3-Methoxy-6-methyl phthalalyl acetic acid

3-Methoxy-6-methyl phthalic anhydride (21.29 g; 0.11 mole) was treated with freshly fused potassium acetate (16.7 g) and acetic anhydride (35 ml). The resulting mixture was heated for 1 hr. at 100°C and then for a further 4 hrs. at 150°–5°C. After cooling water (100 ml) was added and the dark precipitate filtered and washed well with cold water and methanol until the filtrate was almost colourless; the solid was extracted with 5% aqueous sodium bicarbonate (500ml) and the filtered extract acidified. A pale yellow precipitate of the phthalalylacetic acid separated in quantitative yield, m.p. (dioxan) 260°–2°C (d). (Found; C, 61.13; H, 4.40; $C_{12}H_{10}O_5$ requires; C, 61.54; H, 4.30%).

b. 4-Methoxy-7-methyl indane-1,3-dione

Sodium methoxide [from sodium (10.8g)] in methanol (100 ml) was added with vigorous shaking to a solution of 3-methoxy-6-methyl phthalalyl acetic acid (10.8 g; 0.046 mole) in methanol (250 ml) and the mixture stood at ambient temperature for 2 hrs. The resulting orange gel was heated for 5 hrs. at 100°C, cooled and then filtered. On addition of hot (80°C) 5N hydrochloric acid (160 ml) spontaneous decarboxylation ensued and an orange-yellow solid formed. Filtration and recrystallisation (benzene) afforded the indanedione, m.p. 172°C as a buff solid. (Found; C, 69.50; H, 5.34; $C_{11}H_{10}O_3$ requires; C, 69.46; H, 5.30%).

c. 4-Methoxy-7-methyl-2-nitro indane-1,3-dione

Treatment with 4-methoxy-7-methyl indane-1,3-dione with fuming nitric acid as in Example 1(b) gave the 2-nitro derivative as a yellow solid, m.p. (water, hydrochloric acid) 143°–146°C. (Found; C, 56.61; N, 3.93; N, 5.80; $C_{11}H_9NO_5$ requires; C, 56.18; H, 3.86; N, 5.96%).

EXAMPLE 7 a. 5-Bromo indane-1,3-dione

A solution of 4-bromo phthalic anhydride (4.15 g; 0.018 mole) in acetic anhydride (10 g) containing triethylamine (4 g) was treated at room temperature with ethyl acetoacetate (2.38g; 0.02 mole). After 24 hrs. with stirring, crushed ice (20 g) and concentrated hydrochloric acid (10 ml) were added and the precipitated red solid filtered. Addition of a hot (70°–80°C) solution of hydrochloric acid (150 ml) in water (750 ml) to this solid resulted in decarboxylation and generation of 5-bromo indane-1,3-dione as red plates, m.p. (acetone) 152°–3°C. (Found; C, 48.04; H, 2.17; Br, 35.63; $C_9H_5Br O_2$ requires; C, 48.05; H, 2.24; Br, 35.52%).

b. 5-Bromo-2-nitro indane-1,3-dione

Nitration as described in Example 1(b) converted 5-bromo indane-1,3-dione to its 2-nitro derivative, m.p. (water, hydrochloric acid) 127°–9°C. (Found; C, 40.03; H, 1.55; N, 5.11, Br, 29.32; $C_9H_4Br NO_4$ requires; C, 40.01, H, 1.49; N, 5.18; Br, 29.58%).

EXAMPLE 8 a. 4-Bromo indane-1,3-dione

A modification of the procedure used in Example 7(a) in which ethyl acetoacetate was replaced by t-butyl acetoacetate afforded 4-bromo indane-1,3-dione from the anhydride, decomposes above 120°C.

b. 4-Bromo-2-nitro indane-1,3-dione

This was prepared as for the 5-bromo isomer m.p. (water, hydrochloric acid) 127°–8°C. (Found; C, 40.16; H, 1.60; N, 5.36; Br, 28.65; $C_9H_4Br NO_4$ requirements; C, 40.01; H, 1.49; N, 5.18; Br, 29.58%).

EXAMPLE 9 a. 4-Fluoro indane-1,3-dione

Using the procedure outlined in Example 8a gave 4-fluoro indane-1,3-dione m.p. (benzene) 117°–118°C from 4-fluoro phthalic anhydride. (Found; C, 65.87; H, 3.15; $C_9H_5FO_2$ requires; C, 65.86; H, 3.07%).

b. 4-Fluoro-2-nitro indane-1,3-dione

The title compound was formed by nitration of 4-fluoro indane-1,3-dione at 10°C, m.p. (water, hydrochloric acid) 124°C. (Found; C, 47.75; H, 2.68; N, 6.19; $C_9H_4F NO_4.H_2O$ requires; C, 47.59; H, 2.66; N, 6.17%).

EXAMPLE 10 a. 4,5,6,7-Tetrachloro indane-1,3-dione

Tetrachloro phthalic anhydride was converted to the indane dione by the method described in Example 8(a), decomposes on heating. (Found; C, 39.01; H, 0.75; Cl, 50.15; $C_9H_2Cl_4O_2$ requires: C, 38.07; H, 0.71; Cl, 49.60%).

b. 2-Nitro-4,5,6,7-tetrachloro indane-1,3-dione

Nitration of 4,5,6,7-Tetrachloro indane-1,3-dione at 10°C afforded the 2-nitro derivative, m.p. (water, hydrochloric acid) 184°–5°C. (Found; C, 27.89; H, 1.40; N, 3.41; $C_9H Cl_4NO_4.3H_2O$ requires; C, 28.22; H, 1.84; N, 3.66%).

EXAMPLE 11 a. Dimethyl 3,6-dihydro-4,5-dimethyl phthalate 2,3-dimethyl butadiene (30 g; 0.366 mole) and dimethyl acetylene dicarboxylate 47.69 0.366 mole) were heated to 140°C in an autoclave and maintained at the temperature for 4 hrs. After cooling ether was added and the solution filtered. Evaporation of the filtrate afforded the title compound which was recrystallised from methanol; light petroleum (40–60), m.p. 71°–72°C (Found; C, 64.41; H, 7.16; $C_{12}H_{16}O_4$ requires; C, 64.27; H, 7.19%).

b. Dimethyl 4,5-dimethyl phthalate

The above dihydro aromatic compound (50 g.) was added to 10% palladium on charcoal (2.5 g.) and the mixture aerated at 220°–225°C for 3 hrs. After cooling ether was added and the mixture filtered. Evaporation and distillation afforded dimethyl 4,5-dimethyl phthalate, m.p. (methanol, light petroleum (40–60) ) 53°–4°C. (Found: C, 64.87; H, 6.36; $C_{12}H_{14}O_4$ requires: C, 64.85; H, 6.35%).

c. 5,6-Dimethyl indane-1,3-dione

Dimethyl 4,5-dimethyl phthalate (14.6 g; 0.066 mole) in ethyl acetate (20 ml.) was added to a 50% dispersion of sodium hydride in mineral oil (4.63 g; 0.096 mole of NaH) and the mixture refluxed for 4 hrs. on a steam bath. After cooling the yellow solid was filtered and washed with a little cold ethyl acetate. Treatment with a hot (80°C) solution of concentrated hydrochloric acid (20 ml.) in water (200 ml.) for 7 mins. gave the title compound m.p. (benzene) 159°C. (Found: C, 75.77; H, 5.79; $C_{11}H_{10}O$ requires: C, 75.84; H, 5.79%).

d. 5,6-Dimethyl-2-nitro-indane-1,3-dione 5,6-dimethyl indane-1,3-dione (0.52 g; 0.003 mole) suspended in anhydrous ether (5 ml.) was stirred at 10°C during the dropwise addition of fuming nitric acid (1.0 ml.). After the addition was complete the mixture was stirred at ambient temperature for 1 hr. and the precipitated yellow solid filtered. m.p. (water, hydrochloric acid) 111°–113°C. (Found: C, 60.11; H, 4.10; N, 6.14; $C_{11}H_9NO_4$ requires: C, 60.28; H, 4.14; N, 6.39%).

EXAMPLE 12 a. 4-Isopropyloxy indane-1,3-dione

Dimethyl 3-isopropyloxy phthalate (41.93 g; 0.166 mole) in ethyl acetate (55 ml) was cautiously added to a 50% dispersion of sodium hydride in mineral oil (11.0 g; 0.228 mole of NaH) and the mixture refluxed for 4 hours on a steam bath. A yellow solid separated which, after cooling, was filtered and washed with a little ethyl acetate. Addition of this solid to 1N hydrochloric acid at 80°C caused immediate dicarboxylation which was complete within 10.15 mins.

After cooling and filtration, recrystallisation (benzene, petroleum (40°–60°) afforded the title product, m.p. 69°–70°C (Found: C, 70.88; H, 5.93; $C_{12}H_{12}O_2$ requires: C, 70.58; H, 5.92%).

b. 4-Isopropyloxy-2-nitro-indane-1,3-dione

4-Isopropyloxy indane-1,3-dione (0.16 g; 0.003 mole) suspended in dry ether (5 ml) was treated dropwise and with stirring with fuming nitric acid (1.0 ml) at 10°C. The resulting dark solution was treated with 5N hydrochloric acid and evaporated to a yellow crystalline product; m.p. (water, hydrochloric acid) 80°–81°C. (Found: C, 57.94; H, 4.43; N, 5.46; $C_{12}H_{11}NO_5$ requires: C, 57.83; H, 4.45; N, 5.62%).

EXAMPLE 13 a. 4,6 Dimethyl indane-1,3-dione

Dimethyl 3,5-dimethyl phthalate (15.1 g; 0.068 mole) in ethyl acetate (22 ml.) was treated with a 50% dispersion of sodium hydride in mineral oil (4.80 g; 0.10 mole of NaH) and the mixture refluxed for 4 hrs. at 100°C. After filtration the resulting yellow sodium salt was treated for 7 mins. at 70°–80°C. with hydrochloric acid (11.0 ml.) in water (110 ml.) and the dione product filtered and recrystallised. m.p. (benzene) 137°–138°C. (Found: C, 75.73; H, 5.67; $C_{11}H_{10}O_2$ requires: C, 75.84; H, 5.79%).

b. 4,6-Dimethyl-2-nitro-indane-1,3-dione 4,6-Dimethyl indane-1,3-dione (0.52 g; 0.003 mole) suspended in anhydrous ether (5 ml.) was nitrated to the title product as described in Example 12 m.p. (water, hydrochloric acid) 111°–112°C, (Found: C, 60.12, H, 4.16; N, 6.14; $C_{11}H_9NO_4$ requires: C, 60.28; H, 4.14; N, 6.39%).

EXAMPLE 14 a. Benz (e) indane-1,3-dione

To a 50% dispersion of sodium hydride in mineral oil (4.55 g) was added to a solution of diethyl naphthalene 1,2-dicarboxylate (18.5 g) in ethyl acetate (22 ml.) and the mixture refluxed for 3.5 hrs. on a steam bath. After cooling the precipitated orange solid was filtered and decarboxylated with hydrochloric acid (35 ml.) in water (350 ml) at 70°C over 7 mins. to yield benze(e) indane-1,3-dione, m.p. (benzene) 178°C (decomp.) (Found: C, 79.21; H, 4.22; $C_{13}H_8O_2$ requires: C, 79.58; H, 4.11%).

b. 2-Nitro benz(e)indane-1,3-dione

Nitration of benz(e) indane-1,3-dione as described in Example 12 afforded the 2-nitro derivative as an orange crystalline solid, m.p. (water, hydrochloric acid) 134.5°–135.5°C. (Found: C, 64.76; H, 2.91; N, 5.59; $C_{13}H_7NO_4$ requires: C, 64.74; H, 2.93; N, 5.81%).

EXAMPLE 15 a. 3,6-Dimethyl phthalalyl acetic acid 3,6-Dimethyl phthalic anhydride (m.p. 144°–5°C; 15.3 g; 0.087 mole) was treated with freshly fused potassium acetate (13.3 g) and acetic anhydride (27 ml) and heated at 100°C for 1 hr. The mixture was then heated to 150°–155°C at which temperature it was maintained for 4 hours. After cooling, water (80 ml) was added and the brown solid filtered off and washed well with water and cold methanol, After extraction of the residue with 5% sodium bicarbonate followed by acidification of the extract, the title compound was isolated as a yellow solid, m.p. (dioxan) 264°–5°C (Found: C, 66.04; H, 4.69; $C_{12}H_{10}O_4$ requires: C, 66.05; H, 4.62%).

b. 4,7-Dimethyl indane-1,3-dione

Sodium methoxide (from sodium 8.05 g in methanol (80 ml) ) was added with vigorous stirring to a solution of 3,6-dimethyl phthalalyl acetic acid (7.5 g) in methanol (200 ml) and the gel allowed to stand for 2 hrs. The red suspension was then refluxed for 5 hours on a steam bath, cooled and filtered. Addition of the solid to hot (80°C) 5N hydrochloric acid (120 ml) caused immediate decarboxylation and generation of the dione. After cooling the indane dione was filtered, dried, recrystallised, m.p. (benzene) 187°–188°C (Found: C, 75.48; H, 5.88; $C_{11}H_{10}O_2$ requires: C, 75.84; H, 5.79%).

c. 4,7-Dimethyl-2-nitro-indane-1,3-dione 4,7-Dimethyl indane-1,3-dione (0.52 g; 0.003 mole) in dry ether (5 ml) was nitrated with fuming nitric acid (1.0 ml) as described in Example 12 to give 4,7-dimethyl-2-nitro-indane-1,3-dione, m.p. (water, hydrochloric acid) 108°–110°C, (Found: C, 60.07; H, 4.20; N, 6.29; $C_{11}H_9NO_4$ requires: C, 60.28; H, 4.14; N, 6.39%).

EXAMPLE 16 a. Dimethyl-3-ethyl phthalate

Dimethyl acetylene dicarboxylate (26.0 g; 0.183 mole) was added to a solution of 1,3-hexadine (15.0 g; 0.183 mole) in dry benzene (100 ml) and the mixture stirred in an autoclave at 65°C for 24 hours. Evaporation and distillation then afforded the dihydro aromatic adduct as a colourless oil $bp_{0.3\ mm\ Hg.}$ 80°–100°C. Aeration of this at 220°–225°C in the presence of 10% palladinised charcoal over 3 hours then afforded, after spinning bend separation, the title compound as a colourless oil $bp_{1.2\ mm\ Hg.}$ 126°C; (Found: 64.46; H, 6.46; $C_{12}H_{14}O_4$ requires: C, 64.85; H, 6.35%).

b. 4-Ethyl indane-1,3-dione

A solution of dimethyl 3-ethyl phthalate (7.38 g; 0.033 mole) in ethyl acetate (10 ml) was added to a 50% dispersion of sodium hydride in mineral oil (2.32 g) and the mixture reluxed for 4 hours on a steam bath. After cooling the yellow sodium salt was filtered, washed well with dry ether and dried. Treatment with a hot (80°C) solution of hydrochloric acid (10 ml) in water (100 ml) over 10 mins. then gave the requisite dione; m.p. (benzene) 148°C; (Found: C, 76.65; H, 5.45; $C_{11}H_{10}O_2$ requires: C, 75.85; H, 5.80%).

c. 4-Ethyl-2-nitro indane-1,3-dione

A suspension of 4-ethyl indane-1,3-dione (0.52 g; 0.003 mole) in dry ether (5 ml) was treated dropwise at 10°C with fuming nitric acid (1.0 ml) and the precipitated product filtered after 40 mins. at room temperature; m.p. (water, hydrochloric acid) 98°–100°C; (Found; C, 59.98; H, 4.18; N, 6.34; $C_{11}H_9NO_4$ requires: C, 60.28; H, 4.14; N, 6.39%).

EXAMPLE 17 a. 4-Methoxy-6-methyl indane-1,3-dione

Dimethyl 3-methoxy-5-methyl phthalate (14.8 g: 0.062 mole) in ethyl acetate (20 ml) was added to a 50% dispersion of sodium hydride in mineral oil (4.1 g; 0.085 mole) and the mixture refluxed for 4 hours at 100°C. Addition of ether, ethyl acetate to the residual cooled oil afforded a yellow solid which was filtered. Treatment of this solid with 5N hydrochloric acid (30 ml) at 70°C during 7 mins. afforded the title product m.p. (benzene) 172°–3°C (Found: C, 69.45; H, 5.43; $C_{11}H_{10}O_3$ requires; C, 69.46; H, 5.30%).

b. 4-Methoxy-6-methyl-2-nitro indane-1,3-dione

A suspension of 4-methoxy-6-methyl indane-1,3-dione in dry ether was nitrated as in Example 16c to yield the 2-nitro derivative; m.p. (water, hydrochloric acid) 156°–57°C. (Found: C, 56.00; H, 3.86; N, 5.90; $C_{11}H_9NO_5$ requires; C, 56.16; H, 3.86; N, 5.96%).

EXAMPLE 18 a. 6-Ethyl-4-methoxy indane-1,3-dione

Claisen condensation of dimethyl 5-ethyl-3-methoxy phthalate (m.p. 89°C) as given in Example 16b afforded the title product m.p. (benzene, petroleum [40°–60°C ]) 112°–113°C. (Found: C, 70.60; H, 5.97; $C_{12}H_{12}O_3$ requires: C, 70.57; H, 5.92%).

b. 6-Ethyl-4-methoxy-2-nitro indane-1,3-dione

Nitration of a suspension of 6-ethyl-4-methoxy indane-1,3-dione in dry ether as described in Example 16c gave the 2-nitro derivative, m.p. (water, hydrochloric acid) 116°C; (Found: C, 57.85; H, 4.47; N, 5.77; $C_{12}H_{11}NO_5$ requires: C, 57.83; H, 4.45; N, 5.62%).

EXAMPLE 19 a. 5-Phenyl indane-1,3-dione

A solution of dimethyl 4-phenyl phthalate (bp 0.1 170°–80°C) in ethyl acetate was cyclised to the indane dione as described in Example 16b, m.p. (benzene, petroleum [40°–60°]) 116°C. (Found: C, 80.96; H, 4.70; $C_{15}H_{10}O_2$ requires: C, 81.07; H, 4.54%).

b. 2-nitro-5-phenyl indane-1,3-dione

Nitration of 5-phenyl indane-1,3-dione with fuming nitric acid as described in Example 16c gave 2-nitro-5-phenyl indane-1, 3-dione, m.p. (water, hydrochloric acid) 119°C. (Found: C, 65.54; H, 3.39; N, 4.93; $C_{15}H_9NO_4.1/2\ H_2O$ requies: C, 65.21; H, 3.65; N, 5.07%).

EXAMPLE 20 a. 4-Isobutyloxy indane-1,3-dione a solution of dimethyl 3-isobutyloxy phthalate (26.6 g; 0.1 mole; b.p._{0.1 mm Hg} 140°–144°C in ethyl acetate (34 ml) was treated with a 50% dispersion of sodium hydride in mineral oil (6.64 g; 0.137 mole) and the brown solution refluxed for 4 hours on a steam bath. The bright yellow solid which separated was filtered aand cleaned by trituration with ethanol: ether (3:1). Decarboxylation with 5N hydrochloric acid (45 ml) at 70°C over 10 min. gave the title dione; m.p. (benzene, petroleum [40°–60°]) 65°C. (Found: C, 71.63; H, 6.52; $C_{13}H_{14}O_4$ requires: C, 71.54; H, 6.47%).

b. 4-Isobutyloxy-2-nitro indane-1,3-dione

4-Isobutyloxy indane-1,3-dione (0.654 g; 0.003 mole) suspended in dry ether (5 ml) was treated dropwise with fuming nitric acid (1.0 ml) at 10°C and the clear dark red solution left to stir at room temperature for 1 hour. Evaporation in the presence of 5N hydrochloric acid gave the 2-nitro derivative as a yellow solid, m.p. (water, hydrochloric acid) 75°–77°C. (Found: C, 58.92; H, 5.00; N, 5.48; $C_{13}H_{13}NO_5$ requires: C, 59.31; H, 4.98; N, 5.32%).

EXAMPLE 21 a. 4-n-Butyloxy indane-1,3-dione

Claisen condensation of dimethyl 3-n-butyloxy phthalate (m.p. 48°C) with ethyl acetate as described in Example 16b afforded the title compound, m.p. (benzene, petroleum [40°–60°]) 66°C. (Found: C, 71.41; H, 6.54; $C_{13}H_{14}O_4$ requires: C, 71.54; H, 6.47%).

b. 4-n-Butyloxy-2-nitro indane-1,3-dione

Nitration of 4-n-butyloxy indane-1,3-dione as described in Example 20b afforded the 2-nitro derivative, m.p. (water, hydrochloric acid) 85°C. (Found: C, 59.07; H, 5.13; N, 5.13; $C_{13}H_{13}NO_5$ requrires: C, 59.31; H, 4.98; N, 5.32%).

EXAMPLE 22 a. 4-n-Propyloxy indane-1,3-dione

Claisen condensation of dimethyl 3-n-propyloxy phthalate with ethyl acetate as described in Example 20a afforded 4-n-propyloxy indane-1,3-dione, m.p. (benzene) 94°–95°C. (Found: C, 70.69; H, 6.05; $C_{12}H_{12}O_3$ requires: C, 70.58; H, 5.92%).

b. 2-Nitro-4-n-Propyloxy indane-1,3-dione

Nitration of 4-n-Propyloxy indane-1,3-dione as described in Example 16c gave the 2-nitro derivative, m.p. (water, hydrochloric acid) 114°–115°C. (Found: C, 57.57; H, 4.43; N, 5.48; $C_{12}H_{11}NO_5$ requires: C, 57.83; H, 4.45; N, 5.62%).

EXAMPLE 23 a. 4-Phenyl indane-1,3-dione

Dimethyl 3-phenyl phthalate (15.0 g; 0.055 mole) in ethyl acetate (20 ml) was added to a 50% dispersion of sodium hydride in mineral oil (3.67 g) and the mixture refluxed for 4 hrs. on a steam bath. Separation of the bright yellow solid followed by decarboxylation with a hot (80°C) solution of hydrochloric acid (25 ml) in water (250 ml) over 7 mins. gave the title product, m.p. (benzene) 125°–128°C (Found: C, 80.94; H, 4.69; $C_{15}H_{10}O_2$ requires C, 81.07; H, 4.54%).

b. 2-Nitro-4-Phenyl indane-1,3-dione

Nitration of 4-phenyl indane-1,3-dione as described in Example 16c afforded the 2-nitro derivative, m.p. (water, hydrochloric acid) 119°C; (Found: C, 67.04; H, 3.37; N, 4.96; $C_{15}H_9NO_4$ requires: C, 67.42; H, 3.39; N, 5.24%).

EXAMPLE 24

Biological Results

All of the 2-nitro indane-1,3-dione prepared in the preceding Examples were submitted for biological testing. The test system was the Rat Passive Cutaneous Anaphylaxis (PCA) test described below in (ii).

i. Serum containing heat labile homocytotropic antibody was raised in rats by a method similar to that used by Mota. (I. Mota Immunology 1964, 7,681).

Male Wistar rats of 250–300 g, were injected intraperitoneally with 0.5 ml of *Bordatella pertussis* vaccine (containing $4 \times 10^{10}$ dead organism per ml) and subcutaneously with 0.5 ml of an emulsion of 100 mg. of ovalbumin in 2 ml of saline and 3 ml of incomplete Freunds' adjuvant. Rats were bled by cardiac puncture on day 18, the blood was pooled and separated and serum stored at −20° and thawed only once before use.

ii. The P.C.A. test was similar to that described by Ovary and Bier (A. Ovary and O. E. Bier, Proc. Soc. Exp.. Biol. Med. 1952, 81, 584) and Goose and Blair (J. Goose and A. M. J. N Blair, Immunolgy 1969, 16, 769).

0.1 ml of each of six twofold serial dilutions of the serum in 0.9% saline were injected intradermally into separate sites on the shaved dorsal surface of 250–350 g. Wistar rats. 72 hours later the animals were challenged by i.v. injection of 0.3 ml of 1% ovalbumin mixed with 0.1 ml of a 5% solution of pontamine sky blue dye both in isotonic saline buffered with pH. 7.2 Sorenson buffer (P.B.S.). The rats were killed after 20 minutes and the diameter of the blue wheals at the antibody injection sites were measured. The starting dilution of the serum was adjusted so that there was no response, after challenge, at the site of injection of the highest dilution and a maximum response at the lowest dilution. Typically, six twofold serial dilutions of the serum from ¼ to 1/128 were used.

Compounds were tested for their ability to reduce the diameter of the wheals at the injection sites of dilutions of antibody which on all the controls have less than maximum response. Amounts of the compounds were administered to rats each amount to a test group of six animals at a specified time prior to intravenous challenge with ovalbumin. The diameters of the blue wheals which developed on the tests group of animals were compared with those on a control group of six animals treated in the same way as the test group, but which had not received the compound under test.

% Inhibition of P.C.A. = 100 (1 - a/b)

$a$ = The mean of the sum of the diameters of the wheals produced in the test group of animals at those antibody sites where all the control group of animals gave less than maximum response.

$b$ = The mean of the sum of diameters of the wheals produced in the control group of animals at those antibody sites were all the animals in the group gave less than maximum response.

The preferred method of administration was a solution of the test compound dissolved in pH 7.2 buffer and neutralised with sodium bicarbonate. For those compounds having insoluble sodium salts, the salts were isolated by reaction of the free nitro compound with 2.5N sodium hydroxide and the filtered sodium salt washed free of alkali with water. The dried salts were then administered as a suspension in 1% methyl cellulose.

TABLE I

| TEST COMPOUND | FORM IN WHICH ADMINISTERED | DOSE (mg/kg) | TIME BETWEEN DOSING AND CHALLENGE (MINS) | INHIBITION OF PCA RESPONSE |
|---|---|---|---|---|
| 5-bromo-2-nitroindane-1,3-dione | Solution of Na salt | 25 | 0 | 46 |
| | | 25 | 60 | 87 |
| | | 100 | 0 | 30 |
| | | 100 | 60 | 64 |
| 5-methyl-2-nitroindane-1,3-dione | solution of Na salt | 25 | 0 | 66 |
| | | 25 | 30 | 44 |
| | | 100 | 0 | 100 |
| | | 100 | 30 | 47 |
| 4-methyl-2-nitroindane-1,3-dione | Suspension of Na salt in 1% methyl cellulose | 25 | 0 | 2 |
| | | 25 | 60 | 33 |
| | | 100 | 0 | 6 |
| | | 100 | 60 | 57 |
| 4-methoxy-2-nitroindane-1,3-dione | Suspension of Na salt in 1% methyl cellulose | 25 | 0 | −2 |
| | | 25 | 60 | 25 |
| | | 100 | 0 | 18 |
| | | 100 | 60 | 36 |
| 2-nitro-benz[f] indane-1,3-dione | Suspension of Na salt in 1% methyl cellulose | 25 | 0 | 100 |
| | | 25 | 60 | 37 |
| | | 100 | 0 | 100 |
| | | 100 | 60 | 72 |
| 4-bromo-2-nitroindane-1,3-dione | Suspension of Na salt in 1% methyl cellulose | 25 | 0 | 8 |
| | | 25 | 60 | 24 |
| | | 100 | 0 | −4 |
| | | 100 | 60 | 70 |
| 4,5,6,7-tetrachloro-2-nitroindane-1,3-dione | Solution of Na salt | 25 | 0 | −13 |
| | | 25 | 60 | 9 |
| | | 100 | 0 | −3 |
| | | 100 | 60 | 7 |
| 4-ethoxy-2-nitroindane-1,3-dione | Solution of Na salt | 25 | 0 | 13 |
| | | 25 | 30 | 68 |
| | | 100 | 0 | 76 |
| | | 100 | 30 | 55 |

TABLE I-continued

| TEST COMPOUND | FORM IN WHICH ADMINISTERED | DOSE (mg/kg) | TIME BETWEEN DOSING AND CHALLENGE (MINS) | INHIBITION OF PCA RESPONSE |
|---|---|---|---|---|
| 4-fluoro-2-nitroindane-1,3-dione | Solution of Na salt | 25 | 0 | 48 |
| | | 25 | 30 | 8 |
| | | 100 | 0 | 86 |
| | | 100 | 30 | 30 |
| 4-methoxy-7-methyl-2-nitroindane-1,3-dione | Solution of Na salt | 25 | 0 | 34 |
| | | 25 | 30 | 62 |
| | | 100 | 0 | 36 |
| | | 100 | 30 | 44 |
| 5,6-dimethyl-2-nitroindane-1,3-dione | Suspension of Na salt in 1% methyl cellulose | 25 | 0 | 92 |
| | | 25 | 60 | 48 |
| | | 100 | 0 | 73 |
| | | 100 | 60 | 54 |
| 4-isopropyloxy-2-nitroindane-1,3-dione | Suspension of Na salt in 1% methyl cellulose | 25 | 0 | 23 |
| | | 25 | 30 | 36 |
| | | 100 | 0 | 49 |
| | | 100 | 30 | 51 |
| 4,6-dimethyl-2-nitroindane-1,3-dione | Solution of Na salt | 25 | 0 | 58 |
| | | 25 | 30 | 27 |
| | | 100 | 0 | 69 |
| | | 100 | 0 | 35 |
| 4,7-dimethyl-2-nitroindane-1,3-dione | Suspension of Na salt in 1% methyl cellulose | 25 | 0 | 35 |
| | | 25 | 60 | 16 |
| | | 100 | 0 | 46 |
| | | 100 | 60 | 8 |
| 2-nitrobenz(e)-indane-1,3-dione | Suspension of Na salt in 1% methyl cellulose | 25 | 0 | 16 |
| | | 25 | 60 | 50 |
| | | 100 | 0 | 13 |
| | | 100 | 60 | 47 |
| 4-ethyl-2-nitroindane-1,3-dione | Suspension of Na salt in 1% methyl cellulose | 25 | 0 | −5 |
| | | 25 | 60 | 23 |
| | | 100 | 0 | 1 |
| | | 100 | 60 | 25 |
| 4-methoxy-6-methyl-2-nitroindane-1,3-dione | Solution of Na salt | 25 | 0 | 34 |
| | | 25 | 30 | 31 |
| | | 100 | 0 | 80 |
| | | 100 | 30 | 24 |
| 6-ethyl-4-methoxy-2-nitroindane-1,3-dione | Solution of Na Salt | 25 | 0 | 66 |
| | | 25 | 30 | 37 |
| | | 100 | 0 | 91 |
| | | 100 | 30 | 32 |
| 2-nitro 5-phenyl indane-1,3-dione | Suspension of Na salt in 1% methyl cellulose | 25 | 0 | 58 |
| | | 25 | 60 | 56 |
| | | 100 | 0 | 82 |
| | | 100 | 60 | 36 |
| 4-isobutyloxy-2-nitroindane-1,3-dione | Solution of Na salt | 25 | 0 | 61 |
| | | 25 | 30 | 28 |
| | | 100 | 0 | 78 |
| | | 100 | 30 | 41 |
| 4-n-butyloxy-2-nitroindane-1,3-dione | Solution of Na salt | 25 | 0 | 29 |
| | | 25 | 60 | 43 |
| | | 100 | 0 | 63 |
| | | 100 | 60 | 50 |
| 2-nitro-4-phenyl indane-1,3 indione | Solution of Na Salt | 25 | 0 | 12 |
| | | 25 | 60 | 22 |
| | | 100 | 0 | 8 |
| | | 100 | 60 | 24 |

EXAMPLE 25 a. 4,5-Cyclohexano indane-1,3-dione.

The Claisen condensation of dimethyl tetralin 5,6-dicarboxylate (11.6 g; 0.0465 mole) with ethyl acetate (15 ml.) as described in example 1b, afforded 4,5-cyclohexano indane-1,3-dione as a yellow crystalline compound, m.p. (benzene) 97°–99°C (Found: C, 77.80; H, 5.74; $C_{13}H_{12}O_2$ requires: C, 77.98; H, 6.04%).

b. 4,5-Cyclohexano-2-nitroindane-1,3-dione.

To a stirred suspension of 4,5-cyclohexano indane-1,3-dione (1.0 g; 0.005 mole) in anhydrous ether (8.0 ml.) at −20°C was added fuming nitric acid (1.0 ml.) dropwise. After stirring at 0°–5°C for 1 hr. and then at room temperature for a further 1 hr. water (20 ml.) was added, the ether removed under vacuo and the solution filtered. Addition of concentrated hydrochloric acid to the clear, yellow filtrate afforded the title compound on cooling, m.p. (water, hydrochloric acid) 108°–109°C. (Found: C, 63.67; H, 4.48; N, 5.43; $C_{13}H_{11}NO_4$ requires: C, 63.67; H, 4.72; N, 5.71%).

EXAMPLE 26 a. 4,5-Cyclopentano inane-1,3-dione.

Condensation of dimethyl indane 4,5-dicarboxylate (12.42 g; 0.053 mole) with ethyl acetate as in example 1b gave the dione as a yellow solid, m.p. (benzene, petroleum [40°–60°]) 159°–162°(d). (Found: C, 77.55; H, 5.65; $C_{12}H_{10}O_2$ requires; C, 77.40; H, 5.41%).

b. 4,5-Cyclopentano-2-nitro indane-1,3-dione.

Fuming nitric acid (1.0 ml.) was added dropwise to a stirred suspension of 4,5-cyclopentano indane-1,3-dione (0.95 g; 0.005 mole) in dry ether (8.0 ml.) at 5°–10°C and the mixture stirred at this temperature for 45 mins. Further stirring at room temperature for 1 hr. followed by addition of water (20 ml.), evaporation of ether, and filtration gave a clear, yellow filtrate. Addition of an equal volume of concentrated hydrochloric acid to the latter yielded the 2-nitro derivative as a yellow crystalline solid, m.p. (water, hydrochloric acid) 128°–130°C. (Found: C, 59.96; H, 3.96; N, 5.89: $C_{12}H_9NO_4.1/2H_2O$ requires: C, 60.80; H, 4.20; N, 5.83%).

EXAMPLE 27 a. 5-Methoxy-6-Methyl indane-1,3-dione.

A solution of dimethyl 4-methoxy-5-methyl phthalate (14.21 g; 0.06 mole; m.p. 66°–68°C) in ethyl acetate (20 ml.) was added to a 50% dispersion of sodium hydride in mineral oil (3.95 g; 0.082 mole of NaH) and the mixture refluxed for 4 hrs. The orange-brown sodium salt which separated was broken-up with 1:1 ethanol, ether, filtered and dried in vacuo. Addition of the dried solid to hot (80°C) 5N hydrochloric acid (15 ml.) followed by stirring at 70°C for 7 mins. gave the title dione as a yellow solid, m.p. (benzene) 215°–216°C. (Found: C, 69.11; H, 5.50; $C_{11}H_{10}O_3$ requires: C, 69.46; H, 5.30).

b. 5-Methoxy-6-methyl-2-nitro indane-1,3-dione.

Nitration of 5-methoxy-6-methyl indane-1,3-dione as outlined in examplb 1b gave the 2-nitro derivative as an initially yellow solid which turned orange on dehydration, m.p. 110°C. (Found: C, 56.59; H, 3.83; H, 6.03: $C_{11}H_9NO_5$ requires: C, 56.17; H, 3.86; N, 5.96%).

Biological Data for Compounds not included in Table I

| Test Compound | Form in which administered. | dose (mg./kg.) | Time between dosing and challenge (mins). | Inhibition of PCA response |
|---|---|---|---|---|
| 4-n-propyloxy 2-nitroindane-1,3-dione. | Solution of sodium salt | 25 | 0 | 77 |
| | | 25 | 30 | 37 |
| | | 100 | 0 | 30 |
| | | 100 | 30 | 37 |
| 4,5-cyclohexano 2-nitroindane-1,3-dione | Suspension of Na salt in 1% methyl cellulose | 34 | 0 | 7 |
| | | 34 | 60 | 32 |
| 4,5-cyclopentane 2-nitroindane-1,3-dione. | Suspension of Na salt in 1% methyl cellulose | 25 | 0 | 5 |
| | | 25 | 60 | 34 |
| | | 100 | 0 | 26 |
| | | 100 | 60 | 28 |

We claim:

1. A compound of the formula (I) or a pharmaceutically acceptable non-toxic salt thereof:

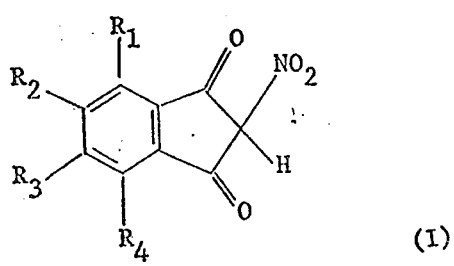

wherein
1 or 2 of $R_1$, $R_2$, $R_3$ and $R_4$ are methyl, ethyl, n-propyl, iso-propyl, n-butyl, sec-butyl, t-butyl, methoxy, ethoxy, n-propoxy, iso-propoxy, n-butoxy, sec-butoxy or t-butoxy and the remaining 2 or 3 are each hydrogen or one of $R_1$, $R_2$, $R_3$ and $R_4$ is fluoro, phenyl or benzyl and the remaining 3 are each hydrogen, or each of $R_1$, $R_2$, $R_3$ and $R_4$ is chloro, or $R_1$ and $R_2$, or $R_2$ and $R_3$, or $R_3$ and $R_4$ taken together are the residue of a 1,2-phenylene ring or a 1,2-cyclohexylene ring.

2. 5,6-Dimethyl-2-nitroindane-1,3-dione or a pharmaceutically acceptable non-toxic salt thereof.

3. 2-Nitrobenz indane-1,3-dione or a pharmaceutically acceptable non-toxic salt thereof.

4. 4-Methoxy-6-ethyl-2-nitroindane-1,3-dione or a pharmaceutically acceptable non-toxic salt thereof.

5. 4-n-Butoxy-2-nitroindane-1,3-dione or a pharmaceutically acceptable non-toxic salt thereof.

6. 4,6-Dimethyl-2-nitroindane-1,3-dione or a pharmaceutically acceptable non-toxic salt thereof.

7. 5-Methyl-2-nitroindane-1,3-dione or a pharmaceutically acceptable non-toxic salt thereof.

8. 4-fluoro-2-nitroindane-1,3-dione or a pharmaceutically acceptable non-toxic salt thereof.

9. The compound according to claim 1 which is 4-methoxy-2-nitroindane-1,3-dione.

10. The compound according to claim 1 which is 4-ethoxy-2-nitroindane-1,3-dione.

11. The compound according to claim 1 which is 4-methoxy-7-methyl-2-nitroindane-1,3-dione.

12. The compound according to claim 1 which is 2-nitro-4,5,6,7-tetrachloroindane-1,3-dione.

13. The compound according to claim 1 which is 4-isopropyloxy-2-nitroindane-1,3-dione.

14. The compound according to claim 1 which is 2-nitro-benz(e) indane-1,3-dione.

15. The compound according to claim 1 which is 4,7-dimethyl-2-nitroindane-1,3-dione.

16. The compound according to claim 1 which is 4-ethyl-2-nitroindane-1,3-dione.

17. The compound according to claim 1 which is 4-methoxy-6-methyl-2-nitroindane-1,3-dione.

18. The compound according to claim 1 which is 2-nitro-5-phenylindane-1,3-dione.

19. The compound according to claim 1 which is 4-isobutyloxy-2-nitroindane-1,3-dione.

20. The compound according to claim 1 which is 2-nitro-4-n-propyloxyindane-1,3-dione.

21. The compound according to claim 1 which is 2-nitro-4-phenylindane-1,3-dione.

* * * * *

UNITED STATES PATENT AND TRADEMARK OFFICE
CERTIFICATE OF CORRECTION

PATENT NO. : 3,936,504
DATED : February 3, 1976
INVENTOR(S) : Derek Richard Buckle et al It is certified that error appears in the above-identified patent and that said Letters Patent are hereby corrected as shown below:

Column 18, line 11    "2-Nitrobenz" should read

--2-Nitrobenz(e)--.

Signed and Sealed this eighteenth Day of May 1976

[SEAL]

Attest:

RUTH C. MASON
Attesting Officer

C. MARSHALL DANN
Commissioner of Patents and Trademarks